United States Patent [19]

Grulke et al.

[11] Patent Number: 5,269,750
[45] Date of Patent: Dec. 14, 1993

[54] TIP UNIT FOR FLUID TRANSFER SURGICAL HANDPIECE

[75] Inventors: David H. Grulke, Battle Creek; Jeffery D. Arnett, Kalamazoo, both of Mich.

[73] Assignee: Stryker Corporation, Kalamazoo, Mich.

[21] Appl. No.: 901,801

[22] Filed: Jun. 22, 1992

[51] Int. Cl.$^5$ ............................................... A61M 1/00
[52] U.S. Cl. .......................................... 604/21; 604/34; 604/902; 362/804
[58] Field of Search ................... 604/21, 30, 34, 35, 604/43, 275, 902; 128/11, 13, 16, 21, 23, 395, 396

[56] References Cited

U.S. PATENT DOCUMENTS

| | | |
|---|---|---|
| Re. 17,319 | 6/1929 | Parkler . |
| 1,556,355 | 10/1925 | Roney ................................... 128/6 |
| 2,243,285 | 5/1941 | Pope ..................................... 128/6 |
| 2,690,744 | 10/1954 | Wallace ................................. 128/6 |
| 2,812,765 | 11/1957 | Tofflemire . |
| 3,071,129 | 1/1963 | Wasserman . |
| 3,089,484 | 5/1963 | Hett . |
| 3,191,600 | 6/1965 | Everett . |
| 3,261,356 | 7/1966 | Wallace . |
| 3,371,202 | 2/1968 | Moore . |
| 3,498,286 | 3/1970 | Polanyi et al. . |
| 3,850,162 | 11/1974 | Iglesias . |
| 3,881,468 | 5/1975 | Foltz ..................................... 128/23 |
| 3,945,375 | 3/1976 | Banko . |
| 4,126,127 | 11/1978 | May ....................................... 128/16 |
| 4,149,315 | 4/1979 | Page, Jr. et al. . |
| 4,204,328 | 5/1980 | Kutner . |
| 4,330,274 | 5/1982 | Friedman et al. . |
| 4,398,885 | 8/1983 | Logé et al. . |
| 4,400,168 | 8/1983 | Buechel et al. . |
| 4,617,013 | 10/1986 | Betz . |
| 4,670,009 | 6/1987 | Bullock ................................. 604/43 |
| 4,759,349 | 7/1988 | Betz . |
| 4,779,130 | 10/1988 | Yabe ...................................... 128/6 |
| 4,872,837 | 10/1989 | Issalene et al. ...................... 604/902 |
| 5,046,486 | 9/1991 | Grulke et al. . |

*Primary Examiner*—Ralph Lewis
*Attorney, Agent, or Firm*—Flynn, Thiel, Boutell & Tanis

[57] ABSTRACT

A tip unit is removably affixed to and extends forward from the barrel of a surgical handpiece, for fluid transfer with respect to the surgical site. The tip unit includes a casing extending forward from the handpiece barrel and a fluid transfer tube extending forward from the casing. The fluid transfer tube extends in sealed relation through axially aligned holes in the front and rear walls of the casing for connection with a fluid transfer unit in the handpiece. A lamp at the far end of the tube is energized by a battery unit in the casing under control of a switch accessible at the outside of the casing. A light transmitting enclosure at the far end of the tube protects against liquid contact with the lamp.

14 Claims, 4 Drawing Sheets

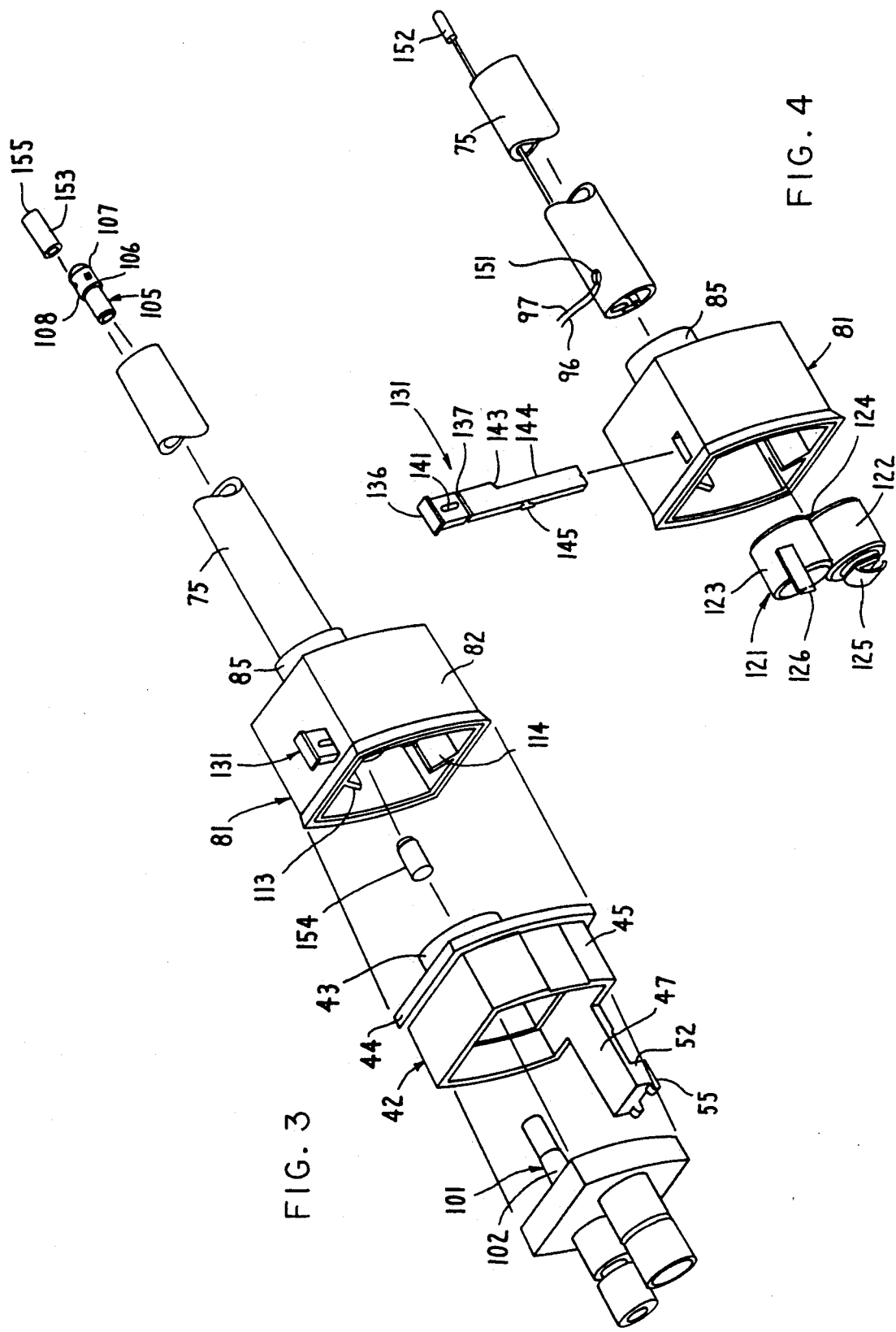

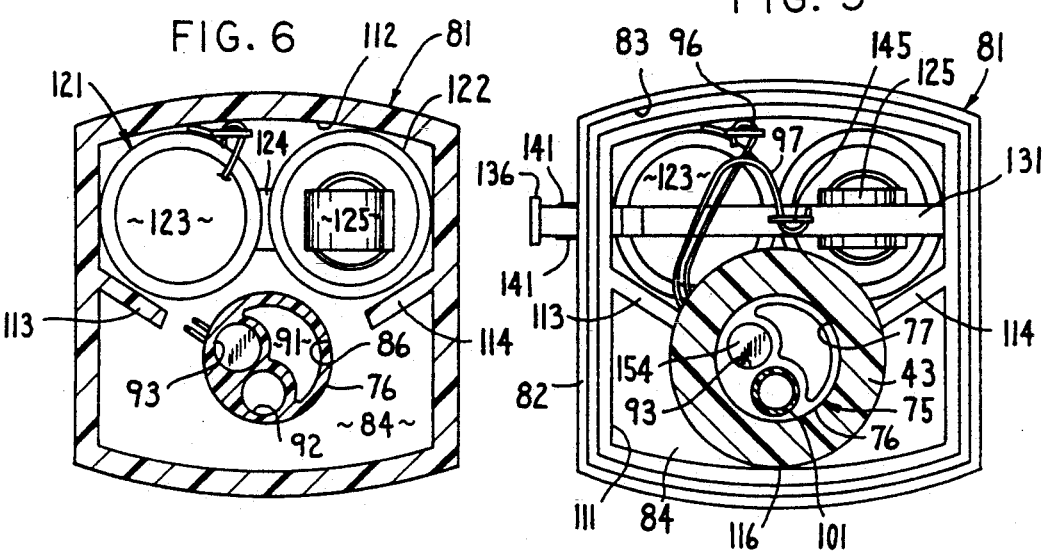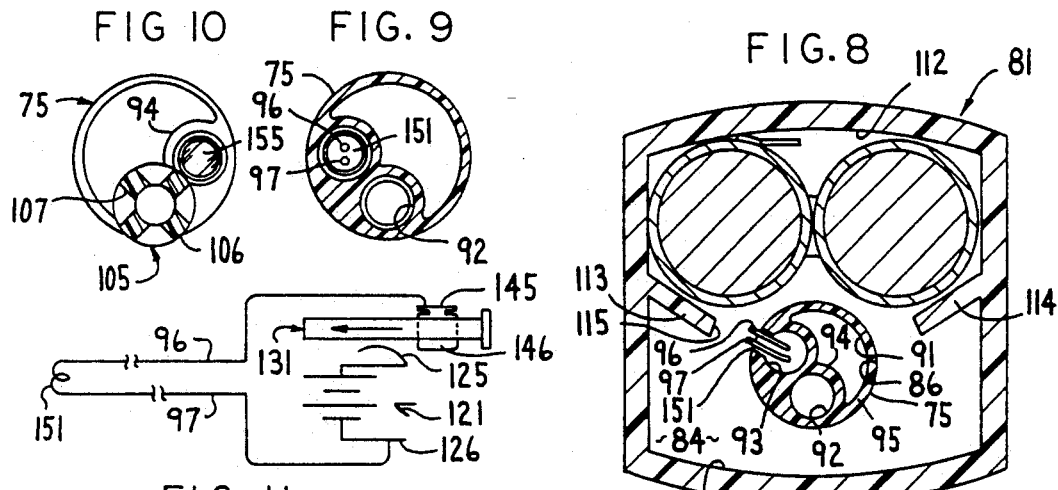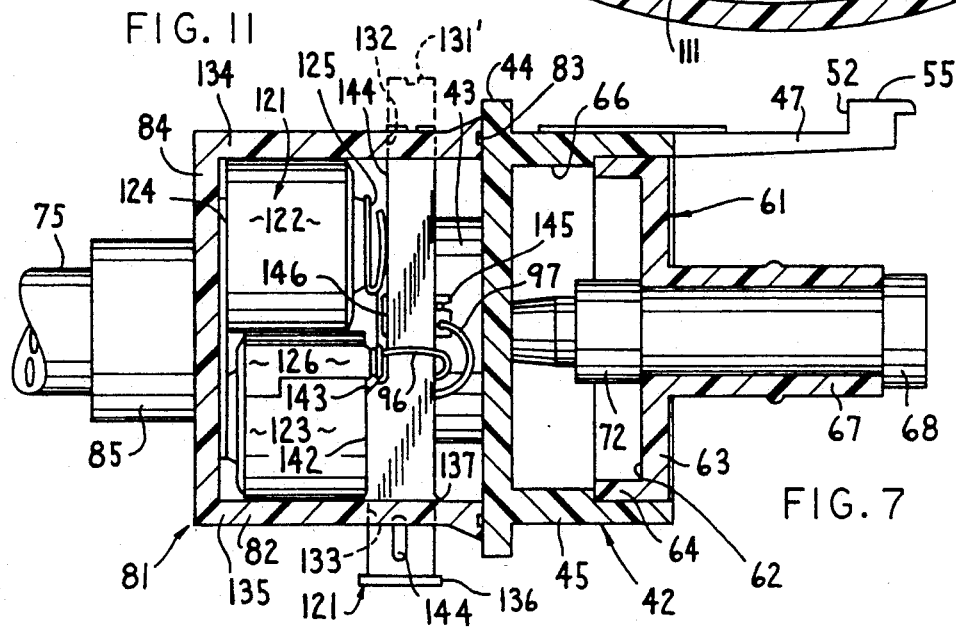

TIP UNIT FOR FLUID TRANSFER SURGICAL HANDPIECE

FIELD OF THE INVENTION

This invention relates to a tip unit for a fluid transfer surgical handpiece and more particularly to a tip unit for a combined suction, irrigation and illumination surgical handpiece.

BACKGROUND OF THE INVENTION

Prior, Grulke et al U.S. Pat. No. 5,046,486, assigned to the assignee of the present invention, discloses a surgical suction/irrigation handpiece including a barrel which at its front end supports a detachable tip unit. The tip unit has a forward extending tube whose front end has suction inlet and irrigation outlet ports for insertion into a surgical site. The irrigation outlet port supplies irrigation liquid to the surgical site to loosen and place in suspension bits of debris produced in the surgical site during surgery. The thus liquid-suspended debris can be then removed from the surgical site by the suction portion of the tip unit and handpiece. The handpiece disclosed in this prior patent includes a pulsing pump to provide a sharply pulsed irrigant liquid flow, which has been found particularly advantageous in loosening debris at the surgical site so that such debris can be placed in liquid suspension and drawn off by the suction portion of the handpiece.

Kutner U.S. Pat. No. 4,204,328 provides a light bulb near the far end of an aspirating tip. However, this prior device exposes its bulb to breakage with risk of leaving glass fragments in the surgical site; shadows its light output by its aspiration tip which extends far forward from the bulb and bends partway around the bulb; locates the bulb and associated wiring and battery and switch outside the fluid transfer tube in a bulky, space-consuming "side saddle" position; locates its bulb far from the central aspiration axis; and directly exposes tissue in the surgical site to the heat of the bulb.

Prior Betz et al. U.S. Pat. Nos. 4,617,013 and 4,759,349 provide suction or suction/irrigation handpiece tips with illumination by light transmitting optical fiber or rod extending the length of the suction or suction/irrigation tip unit for transmitting light to the surgical site from a remote lamp, for example a lamp carried at the rear end of the tip unit. However, transmitting of light from the near end of the handpiece to the far end thereof through an elongate light transmitting rod or bundle of optical fibers may result in loss of illumination intensity and require, in compensation, a higher intensity (thus normally higher heat producing) lamp. Indeed, Betz U.S. Pat. No. 4,759,349, above mentioned, provides at the near end of the tip unit a special heat sink which encloses the lamp and is intended to transfer heat away from it to avoid overheating the handpiece and of the suction/irrigation tip.

The objects and purposes of this invention include provision of illuminated tip unit of suction and/or irrigation kind capable of enhancing removal of debris from surgical sites, including difficult surgical sites such as the femoral canal in a hip replacement or revision surgery, and to provide such a device which overcomes disadvantages in prior devices, such as those above discussed.

Further objects and purposes of the invention will be apparent to persons acquainted with apparatus of this kind upon reading the following specification and inspecting the accompanying drawings.

In one embodiment according to the invention, a tip unit is adapted to extend forward from the barrel of surgical handpiece for fluid transfer with respect to a surgical site, the tip unit comprising a boxlike casing and means for extending the casing forward from the handpiece barrel, and a fluid transfer tube extending unbroken and in sealed relation through axially aligned holes in the front and rear walls of the casing for connection with fluid transfer means of the handpiece.

In another embodiment according to the invention, a tip unit is adapted to extend forward from the barrel of a surgical handpiece for fluid transfer with respect to a surgical site, the tip unit comprising a body, a boxlike casing extending forward from the body, a fluid transfer tube extending forward from the casing, a lamp adjacent the far end of the tube, a switch bar extending laterally through the casing and supported for longitudinal movement in the casing, battery cells fixed together side-by-side laterally in the casing, each cell having a first end facing the wall of the casing and a second end facing the switch bar, a first electrical connection between the first ends of the battery cells adjacent the casing wall, second electrical connection between the second end of one of such battery cell and lamp, and an electrical contact on the second end of the other battery cell. The switch bar has a longitudinally extending side with a first part slidable on a second end of the one cell and a second part slidable on the electrical contact on the second end of the other cell so that the switch bar blocks the battery cells from moving away from the casing wall and thereby fixes the cells in the casing. The switch bar has an electrical contact connected to the lamp and slidably engageable with the electrical contact on the other battery cell.

In still another embodiment of the invention, a tip unit is adapted to extend forward from the barrel of a surgical handpiece for fluid transfer with respect to a surgical site, the tip unit comprising a fluid transfer tube and means for projecting same forward from the handpiece barrel, such tube having internal webs dividing same into longitudinally extending passages, including a suction passage, an irrigation passage, and an electrical conductor guide passage, a lamp within the far end of the tube, and a light transmit enclosure at the far end of the guide passage to seal against entry of liquid into contact with the lamp, the lamp being located just behind the light transmit enclosure to project light forward therefrom where irrigation liquid is expelled from the irrigation passage.

BRIEF DESCRIPTION OF THE DRAWINGS

FIG. 3 is an exploded pictorial view of the tip unit of FIG. 2.

FIG. 4 is an exploded pictorial view of a portion of the FIG. 3 apparatus, including the casing and tubular barrel extension.

FIG. 5 is an enlarged sectional view substantially taken on the line 5—5 of FIG. 2.

FIG. 6 is an enlarged sectional view substantially taken on the line 6—6 of FIG. 2.

FIG. 7 is an enlarged sectional view substantially taken on the line 7—7 of FIG. 2.

FIG. 8 is an enlarged sectional view substantially taken on the line 8—8 of FIG. 2.

FIG. 9 is an enlarged sectional view substantially taken on the line 9—9 of FIG. 2.

FIG. 10 is an enlarged sectional view substantially taken on the line 10—10 of FIG. 2.

FIG. 11 is a schematic electric circuit diagram of the FIG. 1 apparatus.

FIG. 12 is a schematic fluid diagram of the FIG. 1 apparatus.

DETAILED DESCRIPTION

Figure 1:
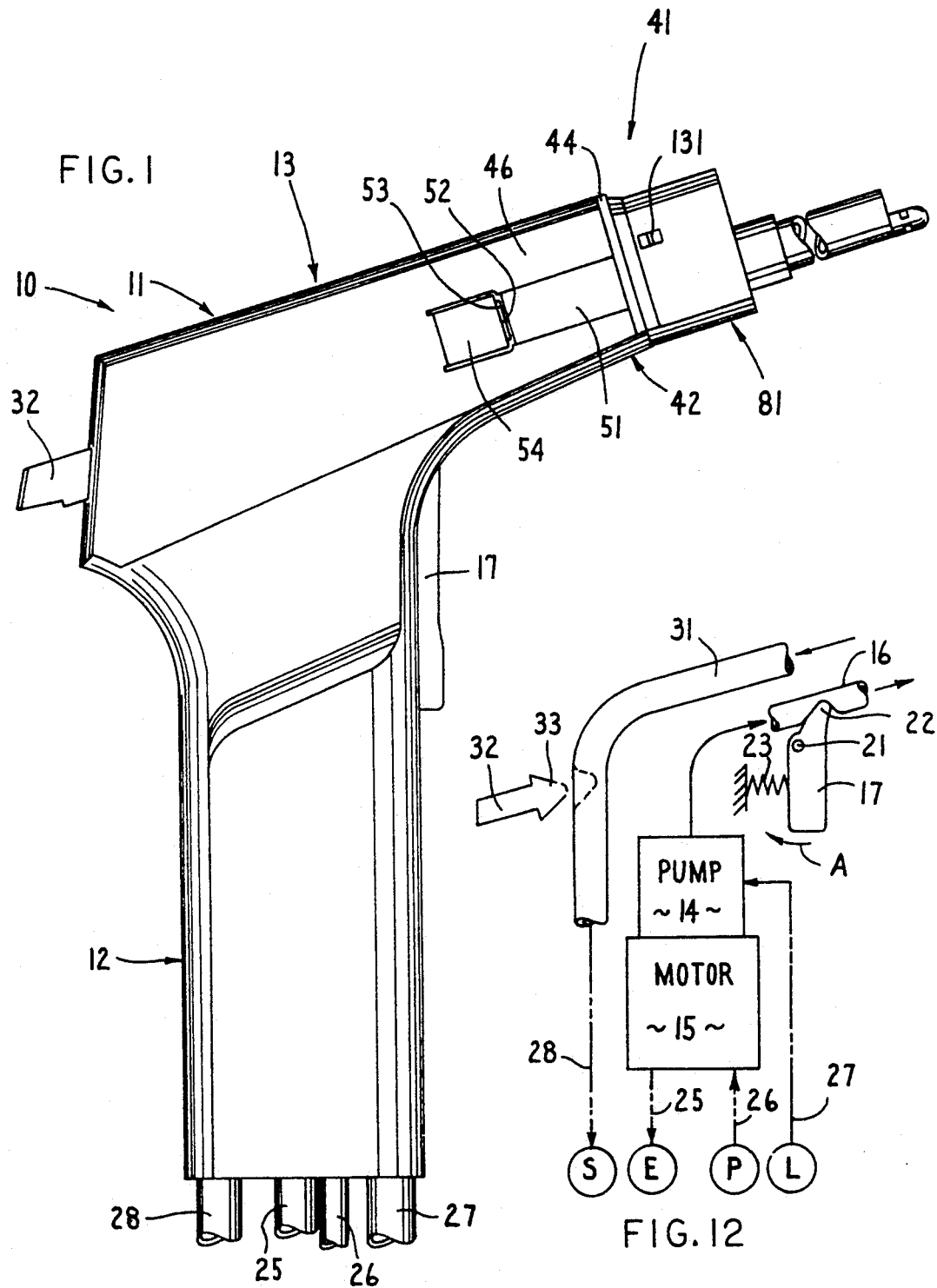
FIG. 1 is a fragmentary side elevational view of a surgical suction/irrigation handpiece embodying the invention.

A handpiece 10, embodying the invention, includes a hollow housing 11 comprising a hand grippable handle 12 surmounted by forward extending barrel 13.

In the particular embodiment shown, the handle 12 contains a pulsing pump 14 (FIG. 12) driven by a motor 15 energized by a continuous feed of gas under pressure through a suitable pressure gas line from a pressure gas (preferably compressed nitrogen) source P, exhaust gas from the motor 15 being taken through an exhaust line 25 to a suitable exhaust port or muffler E. The pump 14 draws irrigation liquid through a line 27 from a source L and provides a pulsed irrigation liquid output through a pinchable tube 16. A trigger 17 is pivoted on a housing 11 at 21 and has an upstanding finger 22. A compression spring 23 backed by the housing 11 bears against the backside of the trigger 17 and normally pivots same to its position shown in FIG. 12 in which the upstanding finger 22 pinches off the tube 16 to prevent forward flow of irrigation liquid therethrough. Upon manual squeezing of the trigger 17, to displace same rearwardly in the direction of the arrow A in FIG. 12, the finger 22 releases the tube 16, opening the latter to pulsed irrigation liquid flow forwardly (rightwardly in FIGS. 1 and 12) therethrough.

The housing 11 also encloses a pinchable suction tube 31. The bottom of the suction tube 31 is communicated through line 28 with a suitable suction source S, such as a hospital operating room wall mounted vacuum port, not shown. A thumb button 32 is slidably mounted on the housing 11 behind the pinchable suction tube 31. Upon forward movement of the thumb button 32 by the user, the forward end 33 of the thumb button presses against and pinches the suction tube 31 to a desired extent to shut off or diminish the suction at the forward end thereof.

A tip unit 41 (FIG. 2) comprises a hollow boxlike body 42 (FIGS. 2 and 3) open at its rear and having a hollow cylindrical boss 43 extending from and opening through the front wall 44 thereof. The body 42 has a perimeter wall 45 (FIG. 3) which extends rearward from the front wall 44 thereof and is snugly rearwardly slidably receivable in the open front end portion of the housing barrel 13 in the manner shown in FIG. 1. The body front wall 44 extends radially outward somewhat beyond the perimeter wall 45 to form a flange which stops against the front end of the housing barrel 13. A resiliently bendable latch leaf 47 (FIG. 3) extends rearward from one side of the perimeter wall 45 of the body 42 and is receivable inside the forward portion of the barrel 13 behind an embossed area 51 (FIG. 1). The latch leaf 47 has an outward, forward facing step 52 (FIGS. 1 and 3) located to catch behind a rear facing step 53 (FIG. 1) in the side of the housing barrel 13 to prevent unintended removal of the tip unit 41 from the front of the housing barrel 13. However, inward pushing of a push button 54 resiliently mounted on the side of the barrel 13 just outside the rear end portion 55 of the latch leaf 47, pushes the latch leaf end portion 55 inward of the housing barrel 13 to disengage the steps 52 and 53 and allow the tip unit 41 to be removed from the front end of the housing barrel 13.

Figure 2:
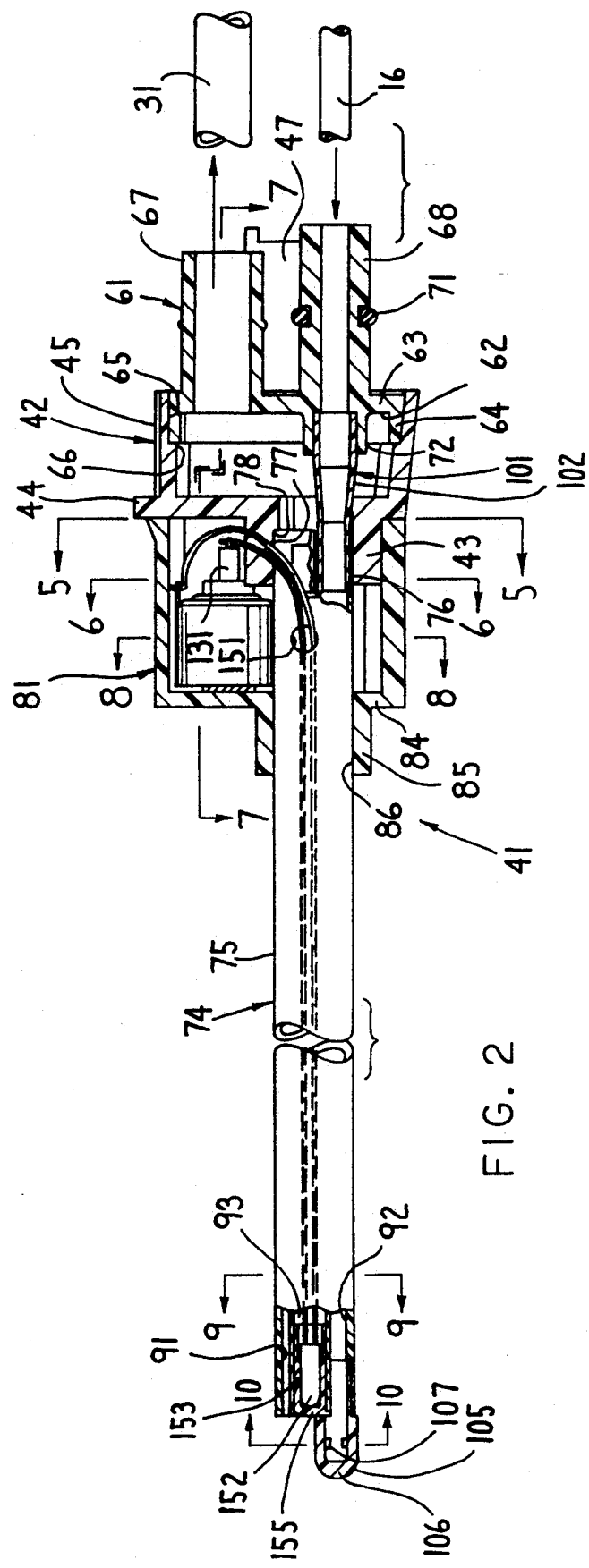
FIG. 2 is a fragmentary, enlarged, partially broken (in central cross-section) elevational view of the tip unit of FIG. 1.

The tip unit 41 further includes an insert 61 (FIGS. 3 and 7). The insert 61 is telescoped partly in the rear portion of the body 42. More particularly, the insert 61 comprises a forward facing recess 62 defined by a radially extending wall 63 from which rearwardly extends a perimeter flange 64. The latter tapers rearward slightly to snug fit in a corresponding tapered recess in the rear portion of the perimeter wall 45 of the body 42. In this way, the hollow body 42 contains a chamber 66 defined by the front wall 44 and perimeter wall 45 of the body 42 and the wall 63 of the insert 61 (FIG. 2).

A hollow tubular suction boss 67 extends rearward integrally from and opens forwardly through the insert wall 63. The suction boss 67 is operatively connected to the suction tube 31 above described, by any convenient means not shown, such as by sleeving the tube 31 over the boss 67.

A hollow tubular irrigation liquid boss 68 extends integrally rearwardly from and opens through the wall 63 of the insert 61 and is connected, by any convenient means not shown, such as by sleeving over with the irrigation liquid tube 16. Alternatively, if desired, a suitable adapter not shown may be used to connect the tube 16 to the boss 68 wherein an O-ring 71 may be used to help effect a seal therebetween. The hollow irrigant liquid boss 68 communicates coaxially with a short hollow forward boss 72 extending forward partway into the suction chamber 66.

A tubular barrel extension 74 (FIG. 2) comprises an elongate plastic tube 75 having a circular, cylindrical outer surface with a near end portion 76 which extends snugly rearward into fixed, seated, sealed relation in the forward portion of the central opening 77 of the front facing boss 43 of body 42. The central opening 77 has a forward facing step 78 to limit the extent of rear insertion of the tube 75 thereinto.

To the extent above described, the apparatus is similar to the present assignee's prior apparatus above described and disclosed in U.S. Pat. No. 5,046,486. Indeed, the tip unit 41 (FIG. 2) is interchangeable with the tip unit of the prior device disclosed in U.S. Pat. No. 5,046,486, which tip units are each removably affixable to the front of the barrel 13 of the handpiece 11.

Turning now in more detail to aspects of the tip unit 41 more specifically embodying the present invention, a boxlike, rear opening casing 81 (FIGS. 3 and 7) has a four-sided perimeter wall 82 whose rear edges are fixed, as by adhesive bonding, in circumferentially continuous fashion to the front face of the front wall 44 of body 42 (FIG. 7). In the embodiment shown, to facilitate such adhesive bonding, the rear edge of the casing perimeter wall 82 is provided with a continuous groove 83 (FIG. 5) for receiving adhesive material. Thus, the front body wall 44 closes the open rear end of the casing 81. The body boss 43 (FIGS. 5 and 7) extends, in off center relation, partway into the interior of the casing 81.

The casing 81 has a front wall 84 (FIG. 7). A hollow boss 85 (FIG. 7) extends forward from the casing front wall 84. The casing boss 85 has a central through opening 86 coaxially aligned with and spaced forward of the central opening 77 (FIG. 2) in the body boss 43. The inside diameters, of the outward stepped front part of central opening 77 and the central through opening 86, are the same, for snug substantially sealed reception of the near end portion 76 of the tube 75 through the boss 85 and into the front end of the boss 43 to rearwardly abut the forward-facing step 78 (FIG. 2). The tube 75 is adhesively fixed in the boss 43.

In the preferred embodiment shown, the tube 75 contains three longitudinally extending passages, namely a main passage 91 and two supplemental passages 92 and 93 (FIG. 8).

The supplemental passages 92 and 93 here are of lesser cross-sectional area than the main passage 91. Preferably the secondary passages are of circular cross-section and separated from each other and the main passage 91 by a web 94 integral with the peripheral wall 95 of the tube 75. The main passage 91 is thus of noncircular, almost crescent shaped cross-sectional shape. The main passage 91 and supplemental passages 92 and 93 are respectively used for suction withdrawal of liquid carried debris from a surgical site; supply of irrigating liquid, such as water, which may be pulsed as above discussed with respect to FIG. 12; and routing of insulated electrical conductors 96 and 97 (FIGS. 8 and 11) as discussed in more detail hereafter. The web 94 and hence the passages 91-93 run the length of the tube 75 and open out the ends thereof. The tube 75, including the web 94 is preferably of a flexible clear plastics material. In one preferred embodiment, adapted for cleaning out the femoral cavity prior to installation of a hip replacement spike in a hip revision, the tube is of clear polyvinyl chloride (PVC) and is about 10 inches long. Such tube is flexible enough so that it can with effort be bent back around upon itself into a circular form, but yet stiff enough that it can be pushed downward into a femoral cavity without buckling or kinking. The flexibility allows the tube to gently bend to follow a curved elongate cavity. In the embodiment shown, the tube is about ⅜ inch in outside diameter. Variations in length, diameter, material, stiffness/flexibility and other characteristics are contemplated.

In particular, the suction passage 91 opens through the far (left in FIG. 2) end of the tube 75 for insertion into a surgical site for withdrawing liquid entrained debris therefrom. The near (right in FIG. 2) end of the suction passage communicates through the rear end portion of the central opening of the body boss 43 with the body chamber 66, which forms a plenum for liquid entrained debris. Such liquid entrained debris is withdrawn from such chamber or plenum 66 through the suction boss 67 of the insert 61 and thence through the suction tube 31 (if not pinched closed by the thumb button 32) and through the suction line 28 toward the suction source s. The amount of suction flow can be reduced by pressing the thumb button 32 forwardly to partially or fully pinch the suction tube 31.

In the embodiment shown, the internal diameter of the irrigation passage 92 is less than the inside diameter of the forward boss 72 of insert 61. The front and rear ends of a tapered tubular adapter 101 are sized, in outside diameter, to insert snugly and sealingly in the rear end of the passage 91 and is adhesively bonded in the forward boss 72 of insert 61, the midportion 102 of the tubular adapter 101 being tapered forwardly to achieve the required reduction in the outside diameter of the forward end of the tubular adapter 101 with respect to its rearward end. The rear end of the passage 92 and the forward boss 72 have recesses opening toward each other and corresponding steps opening toward each other to positively prevent endwise motion of the tubular adapter 101, as seen in FIG. 2. Thus, a continuous path for irrigating liquid flow is provided from the output of the pump 14 through pinchable tube 16 and (directly or indirectly) through insert bosses 68 and 72, tapered adapter 101, and passage 92 to the front end of the tube 75, which end is locatable in the surgical site, for delivering irrigating liquid, which may be pulsed, to any desired area in the surgical site.

In the embodiment shown, the front end of passage 92 receives fixedly therein (and preferably in a forward facing recess thereof) the rear end of a tubular irrigating liquid output tip 105 (FIG. 2, 3 and 10). The forward end of the tip 105 forms a cup 106 whose peripheral wall is perforated by circumferentially spaced irrigating liquid outlet holes 107. The rear end of the cup 106 forms a rearward facing step 108 which seats against the front end of the tube 75 to fix the location of the tip 105 with respect to the tube 75.

The various above described telescoped connections of elements which are to be fixed and may be maintained in such fixed and sealed condition by any conventional means, such as adhesive bonding.

The casing 81 (FIGS. 5, 6 and 8) is divided into side-by-side chambers 111 and 112 by an internal wall formed by an angled pair of wings 113 and 114 (FIG. 8) separated by a central space or opening 115. The wings 113 and 114 angle convergently into the chamber 111. The tube 75 of the tubular barrel extension 74 extends, as seen in FIG. 8, rearward into the chamber 111 and extends laterally into the space 115 between the wings 113 and 114. In the embodiment shown in FIG. 5, the rear end portions of the wings 113 and 114 bear at their laterally adjacent edges on the periphery of the boss 43 of the body 42 which latter also snugly abuts at 116 the interior side of the perimeter wall 82 of the casing 81. The three points of contact above described (at 113, 114 and 116) are substantially evenly circumferentially spaced around the outer perimeter of the body boss 43 and thus assist in properly laterally locating the casing 81 on the front wall 44 of the body 42 preparatory to adhesive bonding the two together.

A battery pack 121 (FIGS. 4, 6 and 7) here comprises a pair of cells 122 and 123 of circular cylindrical shape. The cells 122 and 123 are located side by side (perimeter wall to perimeter wall) in the chamber 112 of the casing 81 and are substantially laterally fixed therein by close adjacency with the opposed faces of the casing perimeter wall 82 and wings 113 and 114. The cells 122 and 123 are located so that the forward facing ends thereof are of opposite polarity. The cells 122 and 123 are thus connected in series by fixed, electrically conductive connection (as by welding) to a conductive plate 124, which plate 124 is adapted to lie face-to-face against the front wall 84 of the casing 81. An electrically conductive leaf spring 125 (FIG. 7) is bent in a U-shape with one-half electrically conductively fixed (as by welding) to the central (negative) terminal of the battery cell 122. A plate-like electrical contact 126 is electrically conductively fixed (as by welding) to the positive polarity peripheral wall of the other cell 123 and extends partly beyond the rearward (right in FIG. 7) end thereof.

An elongate switch bar 131 (FIG. 7) extends snugly but laterally slidably through laterally opposed holes 132 and 133 of corresponding cross-section in opposed sidewalls 134 and 135 of the casing 81 (FIG. 7), namely opposed portions of the casing peripheral wall 82. The switch bar 131 is of rectangular cross-section as are the holes 132 and 133 in which it is slidable, to prevent rotation of the switch bar. The switch bar 131 has, at one end, a radially extending flange 136 (FIG. 7) outside the casing wall 135 and, spaced therefrom on the inside of such casing wall 135, a projection 137. The flange 136 and projection 137 limit the maximum longitudinal displacement of the switch bar 131 by colliding with the casing sidewall 135. The same end portion of the switch bar 131 has shallow longitudinal ribs 141 on opposite sides thereof and which engage the sides of the hole 133 in the wall 135 frictionally to frictionally maintain the switch bar 131 in one position unless the user intentionally slides the bar longitudinally.

The forward edge 142 (FIG. 7) of the switch bar 131, within the casing 81, bears slidably on the rear end of the battery cell 123 and extends substantially diametrically across same, as seen in FIGS. 5 and 7, and thereby assists in holding the battery pack 122, 123 against the front wall 84 of the casing 81. The switch bar 131 is stepped at 143 (FIG. 7) in a rearward direction to leave the edge 144 of the switch bar 131 opposing the cell 122 relieved sufficient to allow room for the electrically conductive spring 125 which contacts the thus relieved edge 144 as seen in FIG. 7. The switch bar 131 further includes a blade-like electrical contact 145 which extends forwardly/rearwardly in fixed relation therethrough. A portion 146 of the electrical contact 145 protrudes forwardly through the edge 144. In the "off", outward position of the switch bar 131 shown in FIG. 7, the forwardly protruding portion 146 of the electrical contact 145 lies out of contact with the electrically conductive spring 125 as shown in FIG. 7. However, when the switch bar 131 is pushed inward (upward in FIG. 7) to its inward position generally indicated in broken lines at 131', the forwardly protruding portion 146 of the electrical contact 145 makes electrical contact with the electrically conductive spring 125.

The electrical conductors 96 and 97, which are conventional, insulation-covered conductors, have rear end portions which pass from the tube 75 (more specifically, from the passageway 93) into the interior of the casing 81 through a lateral hole 151 in the side of the tube 75 adjacent the battery cell 123. The insulated rear end portions of the electrical conductors 96 and 97 thus pass from the passageway 93 through the hole 151 into the chamber 112. The end of one such conductor, here the conductor 97, connects in electrically conductive relation to the rear end of the electrical contact 145 on the switch bar 131. The rear end of the other conductor 96 is in electrically conductive contact with the electrical conductor 126 on the side of the cell 123.

The insulated conductors 96 and 97 extend forward from the interior of the casing 81 through the hole 151 and forward along the passage 93 in the tube 75. An electric lamp 152 (FIGS. 2 and 3) faces forward and is snugly fixed within a transparent (or at least efficiently light transmitting) cylindrical cap 153. The cap 153 is generally cup-shaped, having a closed front wall 155 through which the light from the lamp 152 can shine forward in the surgical site. The lamp is fixedly located in the cap 153 by any convenient means, for example by the stiffness of the electrical conductors 96 and 97 extending rearward from the lamp. The cap 153 is fixed in the front (left in FIG. 2) end of the passage 93 in a sealed manner, to prevent entry of liquid into the front end of the passageway 93. The rear end of the passage 93 is sealed by means of a fixed plug 154 (FIGS. 3 and 5), such that the only opening into the passage 93 is the hole 151 (FIG. 8) in the interior of the casing 81. Thus, fluid in the surgical site, aspirated through the passage 91 from the surgical site or injected as irrigating liquid from the source L, cannot enter the passage 93 or come into contact with the electrical conductors 96 and 97 and lamp 152 therein.

Insulation may be stripped from the ends of the electrical conductors 96 and 97 leaving the ends that are bared to engage the electrical contacts 126 and 145 and conventional leads from the lamp 151. It will be understood that the conductors 96 and 97 are insulated over all parts of the length thereof needed to prevent electrical shorting therebetween. Indeed, in the embodiment shown, the rear ends of the wires 96 and 97 are insulated fully but are engaged with conventional electrical terminals 145 and 126 of the type which bite through the insulation into contact with the conductive wire therewithin to establish electrical contact while at the same time rigidly securing the electrical conductors to the contact.

In the preferred embodiment shown, the casing 91 is preferably of medical grade ABS. The switch bar 131 is preferably of medical grade polycarbonate. The irrigation outlet tip 105 and cap 153 are preferably of clear polycarbonate. The tube 75 is preferably of polyvinyl chloride (PVC). The fixed together parts of the apparatus are preferably held together by suitable adhesive such as Loctite ™, Model No. 18013, available from Loctite Corporation located at Birmingham, Mich.

To maximize the working time of the lamp 152, the battery cells 122 and 123 are preferably lithium cells. In the embodiment shown, the cells have useful operating life of about 1.5 hours and are available from Duracell Inc. located at Berkshire Industrial Park, Bethel, Conn. 06801, under Model No. DL 1/3N.

The lamp 152 is capable of a light output of at least 0.1125 M.S.C.P. (mean spherical candle power) and is available from Glolite, located at Pauls Valley, Okla., under Model No. 4-6-92-201-01.

Substitution of equivalent parts is of course contemplated.

OPERATION

The apparatus can be assembled as follows.

The rear end of the tube 75 can be inserted rearward through the casing boss 85 and into the casing 81. The irrigation tip 105 is inserted into the forward end of the irrigation passage 92 of the tube 75. The insulated conductors 96 and 97 are led through the hole 151 in the tube 75 and then forward through the front end of the passage 93 of the tube 75. The ends of the insulated conductors 96 and 97 have been previously stripped and soldered to conventional terminals on the rear of the lamp 152. The lamp 152 then can be sealed in the cap 153 which in turn can be sealed into the front end of the passage 93 of tube 75. The plug 154 is then sealed in the rear end of the passage 93 of tube 75 such that the only opening left in the passage 93 is the hole 151 through which the insulated conductors 96 and 97 are led.

The battery cells 122 and 123 can then be connected by welding to the electrically conductive plate 124 and the electrical terminals 125 and 126 to in effect form a unitary battery pack. This battery pack or unit can then be placed in the casing 81. The switch bar 131 is then inserted through the casing via the holes 132 and 133. This snaps the projection 137 through the hole 133 into the casing to its position shown in FIG. 7. This also sandwiches the battery unit between the switch bar and the forward wall 84 for the casing 81. The insulated conductors 96 and 97 can then have their ends electrically connected to the terminals 126 and 145 of the battery unit.

The insert 61 can now be inserted into and sealed in the rear of body 42. The tubular adapter 101 is sealed by adhesive bonding in the forward boss 72 of insert 61. The body 42 can be moved forward toward the open rear end of casing 81. In this way, the tubular adapter front end sealingly and with adhesive bonding enters the rear of the irrigation liquid passage 92, the rear end of tube 75 seats in body boss 43 in a sealed manner by adhesive bonding, the body boss 43 enters the casing chamber 84 between the ends of the wings 113 and 114 and the opposed part of the casing perimeter wall 82, and the rear end of the casing perimeter wall 82 is bonded against the front body wall 44 to close the previously opened casing rear end.

The resulting tip unit 41 is thus completed and can be snap fitted into the front end of the handpiece barrel 13 like the nonilluminated tip unit shown in above-mentioned U.S. Pat. No. 5,046,486, to connect the irrigation liquid passage 92 to irrigation pump 14 and suction passage 91 to suction tube 31.

The handpiece may be marketed with the exhaust line 25 and a suitable exhaust port or muffler E attached.

Prior to use, the handpiece can be conventionally sterilized, e.g. by ethylene oxide.

Prior to use, the handpiece is connected to a suction source S, pressure gas source P and irrigation liquid source L through the lines 28, 26 and 27, respectively.

The handpiece 10 can be used as follows.

The surgeon or an assistant (hereafter the user) grips the handle 12 of the handpiece 10 and guides the forward end of the tube 75 into a surgical site. For example, in a hip joint revision, after removal of the old hip stem prosthesis, the forward end of the tube 75 may be guided into the femoral cavity to remove the remaining particles of old cement and any other debris. The flexibility of the tube 75 allows it to conform to a curvature in the femoral canal while yet being stiff enough to be pushed forward to the desired depth therein. To illuminate the portion of the femoral canal ahead of the forward end of the tube 75, the user pushes the switch bar 131 (at the flange at 136) longitudinally further into the casing 81, from its FIG. 7 solid line position to its FIG. 7 dotted line position. This moves the electrical contact 145 on the switch bar into contact with the electrically conductive spring 125 on the battery pack 122, 123 and completes a circuit (FIG. 11) through the battery pack and bulb 151 to light the bulb. The switch bar is stable in either its solid line retracted position or dotted line pushed in position of FIG. 7. Thus, the bulb 151 continues to provide light shining forward from the end of the tube 75 until such time as the user may push the opposite end (upper end in FIG. 7) of the switch bar from its dotted line position to its solid line position of FIG. 7 and thereby remove the switch bar contact 145 from engagement with the electrically conductive spring 125 within the battery pack, thereby breaking the circuit of FIG. 11 and extinguishing the lamp 151.

At any time, whether or not the lamp 151 is ignited, the user can supply irrigational liquid (pulsed in the particular example shown) to the surgical site by pulling the trigger 17, displacing the trigger 17 more and more for increasing irrigating liquid flow. In the particular example shown, the suction source is normally fully open to the suction passage 91 in the tube 75. However, the user can reduce the suction capability by pushing to a greater or lesser extent on the thumb button 32.

In the example shown, the entire handpiece 10, as well as the tip unit 41, is disposable after completion of a surgery, thus eliminating any possibility of cross contamination between patients. Accordingly, the battery pack need only have sufficient capacity to maintain ignition of the lamp 152 during a single surgical procedure. In fact, ignition of the lamp 152 often is maintained for only a portion of a given surgical procedure. Nevertheless, the battery pack is given more than enough capacity to handle the need. For example, the battery pack may be capable of one hour illumination of the bulb 152 whereas in a typical hip joint revision use of the lamp 152 typically would not exceed 15 minutes.

In view of the ability to utilize tip units of different kinds (for example, nonilluminated tip units of the kind shown in the aforementioned U.S. Pat. No. 5,046,486, and of the illuminated type shown in the present application) with the same type of handpiece 10, it will be seen that the number of handpieces 10 inventoried can be substantially reduced. Also, tip units of different types (illuminated and nonilluminated, for example) can be inventoried separately from the handpieces 10.

Moreover, surgeons and surgical assistants familiar with installing the nonilluminated tip disclosed in aforementioned U.S. Pat. No. 5,046,486 on a handpiece, will be able, without training, to install the present illuminated tip unit 41 on such a handpiece 10.

By including the switch 131 and battery pack in the exchangeable tip unit 41, the present invention eliminates any need to modify existing handpieces 10 of the kind shown in aforementioned U.S. Pat. No. 5,046,486 and any need for external electrical connections from the tip unit 41 either to the handpiece 10 or any external switch and/or electrical supply.

Moreover, the location of the switch bar 131 on the tip unit 41 places it convenient to the hand of the user. Further, the physical location of the switch bar, protruding either rightwardly from the tip unit casing 81 (as seen by the user with handpiece 10 in the hand in its lamp ignited position or protruding leftwardly from the casing 81 in its lamp off position) as well as the differences in the size and shape of the two exposable ends of the switch bar, allow the user, by touch alone, to determine the status of the lamp 152 or to turn the lamp 152 on or off, without need to even look in the surgical site for a visual cue as to the on or off condition of the lamp.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A tip unit adapted to extend forward from the barrel of a surgical handpiece for fluid transfer with respect to a surgical site, the tip unit comprising:
   a boxlike casing having a front and a rear wall wherein said rear wall is mountable forward of a handpiece barrel;
   a fluid transfer tube having a forward end extending outwardly from said casing front wall and a rear end extending unbroken in sealed relation from said front and rear walls of said casing for connection with fluid transfer means of the handpiece, said casing comprising side-by-side first and second chambers separated by an internal wall, said internal wall having a through opening laterally communicating between said chambers, said fluid transfer tube extending axially through said first chamber adjacent said opening;

an electric load positioned adjacent the forward end of said fluid transfer tube and a battery cell means for connection to said load, said battery cell means being located in said second chamber adjacent said lateral opening, and electric circuit means for energizing said load from said battery cell means;

an elongated switch bar extending laterally through said second chamber past said battery cell means with ends of said switch bar extending through holes in opposite sidewalls of said casing for longitudinal displacement with respect to said casing wherein longitudinal displacement of the switch bar from a first to a second position activates said electric circuit means permitting the flow of electricity from said battery cell means to said load.

2. The apparatus of claim 1 in which said load comprises a lamp located at the forward end of said fluid transfer tube, said electric circuit means further including a contact on said switch bar engageable and disengageable with a contact on said battery cell means for lighting or extinguishing said lamp upon displacement of said switch bar, and connecting means for connecting said lamp between said battery cell means and switch bar contact.

3. The apparatus of claim 2 in which said fluid transfer tube includes therein separate longitudinally extending passages, comprising a fluid passage and an electrical conductor passage separated by a longitudinally extending web, a hole in the side of said tube communicating only with said electrical conductor passage and located in said casing, said connecting means including electrical conductor means extending rearward along said electrical conductor passage from said lamp and laterally out said hole adjacent said battery cell means and switch bar for electrical connection to said battery cell means and switch bar to enable lighting and extinguishing of said lamp by displacement of said switch bar.

4. A tip unit adapted to extend forward from the barrel of a surgical handpiece for fluid transfer with respect to a surgical site, the tip unit comprising:
 a boxlike casing having a front and a rear wall wherein said rear wall is mountable forward of a handpiece barrel;
 a fluid transfer tube having a forward end extending outwardly from said casing front wall and a rear end extending unbroken in sealed relation through said front and rear walls of said casing for connection with fluid transfer means of the handpiece;
 a lamp on said transfer tube;
 a battery cell means in said casing beside said fluid transfer tube, a switch bar extending into said casing, and electric contact means cooperating with said switch bar and said battery cell means, said switch bar being displaceable for engaging the electric contact means to light or extinguish said lamp upon displacement of said switch bar;
 said fluid transfer tube further including therein separate longitudinally extending passages, including a fluid passage and an electrical conductor passage separated by a longitudinally extending web, a hole in the side of said tube communicating only with said electrical conductor passage and located in said casing, electrical conductor means extending rearwardly along said electrical conductor passage from said lamp and laterally out said hole adjacent said battery cell means and said switch bar for electrical connection to said battery cell means, wherein displacement of said switch bar enables said lighting and extinguishing of said lamp.

5. The apparatus of claim 4 in which said battery cell means has first and second opposite polarity electrical contacts wherein said switch bar has an electrical contact engageable with and disengageable from one of said battery cell contacts, said electrical contacts of said battery cell means and switch bar defining said electric contact means.

6. A tip unit adapted to extend forward from the barrel of a surgical handpiece for fluid transfer with respect to a surgical site, the tip unit comprising:
 a boxlike casing having a front and a rear wall wherein said rear wall is mountable to extend axially forward of a handpiece barrel;
 a fluid transfer tube having a forward end extending outwardly from said casing front wall and a rear end extending unbroken in sealed relation through said front and rear walls of said casing for connection with fluid transfer means of the handpiece;
 a hollow body extending rearward from said casing rear wall and defining means for mounting said casing to extend axially forward from a handpiece barrel, said fluid transfer tube having internal webs dividing it into longitudinally extending suction, irrigation, and electrical conductor guide passages, a hole in the side of said tube open between said electrical conductor guide passage and the interior of said casing for routing of electrical conductor means between said casing interior and the forward end of said guide passage, a plug in the rear of said electrical conductor guide passage to close same, an extension tube extending from the rear end of said irrigation passage through said hollow body to an irrigant liquid source of a handpiece, the rear end of said suction passage being open to the interior of said hollow body and means connecting the interior of said hollow body to a suction source of the handpiece.

7. A tip unit adapted to extend forward from the barrel of a surgical handpiece for fluid transfer with respect to a surgical site, the tip unit comprising:
 a body mountable on the barrel of a handpiece;
 a boxlike casing extending forward from said body;
 a fluid transfer tube having a far end extending forwardly and outwardly from said casing;
 a lamp adjacent the far end of said tube;
 a switch bar extending laterally through said casing and supported for longitudinal movement in said casing;
 battery cells fixed together side-by-side laterally in said casing, each cell having a first end facing a wall of said casing and second end facing said switch bar;
 means in said casing, proximate to said switch bar and battery cells, for fluid transfer between said fluid transfer tube and a handpiece;
 a first electrical connection between the first ends of said battery cells adjacent said casing wall;
 a second electrical connection between the second end of one of said battery cells and said lamp;

an electrical contact on the second end of said other battery cell, said switch bar having a longitudinally extending side with a first part slidable on a second end of said one cell and with a second part slidable on said electrical contact on said second end of said other cell so that said switch bar blocks said battery cells from moving away from said casing wall and thereby fixes said cells in said casing, said switch bar having an electrical contact connected through a third electrical connection to said lamp and slideably engageable with said electrical contact on said other battery cell, said second and third electrical connections comprising conductors extending along said tube.

8. The apparatus of claim 7 in which said first electrical connection comprises a conductive plate fixed to and in electrical contact with said cells and backed by said casing wall.

9. The apparatus of claim 7 in which said switch bar side is stepped laterally toward said one cell to compensate for a difference in height of said battery cells caused by said electrical contact on said second end of said other cell.

10. The apparatus of claim 7 in which said switch bar extends snugly and slideably through opposed holes in opposite sides of said casing, projecting means on said switch bar engageable with at least one said side wall of said casing to limit to a specific range the longitudinal sliding of said switch bar with respect to said casing and battery cells.

11. The apparatus of claim 7 in which said casing comprises side-by-side first and second chambers separated by an internal wall, said internal wall having a through opening laterally communicating between said chambers, said fluid transfer tube extending axially through said first chamber adjacent said opening, said opening in said casing internal wall dividing said internal wall into spaced wings, said cells being laterally retained by said wings in said second chamber, said switch bar and first electrical connection and electrical contact being in said second chamber.

12. The apparatus of claim 11 in which said fluid transfer tube includes therein separate longitudinally extending fluid and electrical conductor guide passages separated by a longitudinally extending web, a hole in the side of said tube communicating only with said electrical conductor passage and located in said casing, said electrical conductors extending rearward along said electrical conductor passage from said lamp and laterally out said hole adjacent said battery cells and switch bar for electrically connecting to said battery cell and switch bar to enable lighting and extinguishing of said lamp by displacement of said switch bar.

13. A tip unit adapted to extend forward from the barrel of a surgical handpiece for fluid transfer with respect to a surgical site, the tip unit comprising:
 a boxlike casing having a front and a rear wall wherein said rear wall is mountable forward of a handpiece barrel;
 a fluid transfer tube having a forward end extending outwardly from said casing front wall and a rear end extending unbroken and in sealed relation through the front and rear walls of said casing for connection with fluid transfer means of the handpiece, said box-like casing comprising side-by-side first and second chambers separated by an internal wall, said internal wall having a through opening laterally communicating between said chambers, said fluid transfer tube extending axially through said first chamber adjacent said opening, said casing rear wall having a boss defining said hole in said rear wall and extending forward partway into said first chamber at said opening in said internal wall and receiving said tube, said internal wall being defined by first and second wings angled convergently toward said first chamber and fluid tube, said internal wall further including edges laterally spaced across said opening and bearing on said boss, battery cells laterally retained by said wings in said second chamber and facing said tube through said opening, a lamp carried by said fluid transfer tube, and electric circuit means connecting said battery cells and lamp and including electrical conductors extending from said tube and between said wings to said battery cells.

14. The apparatus of claim 13 including slideable means extending into said second chamber from outside said casing for axially fixing said battery cells in said second chamber, said electrical conductors including a contact on said slideable means engageable with a given said battery cell to light said lamp and carried on said slideable means.

* * * * *

UNITED STATES PATENT AND TRADEMARK OFFICE
CERTIFICATE OF CORRECTION

PATENT NO. : 5 269 750

DATED : December 14, 1993

INVENTOR(S) : David H. GRULKE et al

It is certified that error appears in the above-identified patent and that said Letters Patent is hereby corrected as shown below:

Column 12, line 12; after "contacts" insert ---,---.

line 38; change "rear of said" to ---rear end of said---.

line 60; change "and second" to ---and a second---.

Signed and Sealed this

Twenty-eighth Day of June, 1994

Attest:

BRUCE LEHMAN

*Attesting Officer*     *Commissioner of Patents and Trademarks*